United States Patent [19]

Horrobin et al.

[11] Patent Number: 5,847,000
[45] Date of Patent: Dec. 8, 1998

[54] FATTY ACID DERIVATIVES

[75] Inventors: David F. Horrobin, Guildford; Philip Knowles; Mehar S Manku, both of Carlisle, all of England

[73] Assignee: Scotia Holdings PLC, England

[21] Appl. No.: 828,716

[22] Filed: Mar. 28, 1997

Related U.S. Application Data

[63] Continuation of Ser. No. 388,667, Feb. 17, 1995, abandoned.

[30] Foreign Application Priority Data

Mar. 1, 1995 [GB] United Kingdom .................. 9403855

[51] Int. Cl.$^6$ .......................... A61K 31/375; A61K 9/20; A61K 9/48; C07D 307/62
[52] U.S. Cl. ........................................... 514/552; 514/474
[58] Field of Search ..................................... 514/310, 474, 514/552, 546, 943, 960, 962; 549/315; 424/451, 464

[56] References Cited

U.S. PATENT DOCUMENTS

| | | | |
|---|---|---|---|
| 4,151,178 | 4/1979 | Seib et al. ................. | 549/317 |
| 4,289,702 | 9/1981 | Gruetsmacher et al. ............ | 549/317 |
| 4,388,324 | 6/1983 | Horrobin ................. | 514/747 |
| 4,645,660 | 2/1987 | Takahashi et al. ................ | 530/382 |
| 4,705,869 | 11/1987 | Nickels et al. ............. | 549/317 |
| 4,792,418 | 12/1988 | Rubin et al. ............. | 554/186 |
| 4,818,521 | 4/1989 | Tamabuchi ................. | 424/62 |
| 4,822,898 | 4/1989 | Kamaya et al. ............. | 549/317 |
| 4,882,451 | 11/1989 | Yoshida et al. ............. | 556/440 |
| 4,938,960 | 7/1990 | Ismail ............... | 424/195.1 |
| 4,997,958 | 3/1991 | Pauling et al. ............. | 549/315 |
| 5,071,753 | 12/1991 | Enomoto et al. ............. | 435/126 |
| 5,078,989 | 1/1992 | Ando et al. . | |
| 5,116,624 | 5/1992 | Horrobin et al. ............. | 424/702 |
| 5,122,536 | 6/1992 | Perricone . | |
| 5,574,063 | 11/1996 | Perricone ............. | 514/474 |
| 5,665,769 | 9/1997 | Kato et al. ............. | 514/474 |
| 5,703,122 | 12/1997 | Duffy ............. | 514/474 |
| 5,767,149 | 6/1998 | Yamamoto et al. ............ | 517/474 |

FOREIGN PATENT DOCUMENTS

| | | |
|---|---|---|
| 0 019 423 | 11/1980 | European Pat. Off. . |
| 0 037 175 | 10/1981 | European Pat. Off. . |
| 0 087 864 | 9/1983 | European Pat. Off. . |
| 0 115 419 | 8/1984 | European Pat. Off. . |
| 0 296 483 | 12/1988 | European Pat. Off. . |
| 0 347 664 | 12/1989 | European Pat. Off. . |
| 0 440 307 A2 | 8/1991 | European Pat. Off. . |
| 0 577 305 A1 | 1/1994 | European Pat. Off. . |
| 639776 | 12/1936 | Germany . |
| 1231848 | 1/1968 | Germany . |
| 62-081307 | 4/1987 | Japan . |
| 339632 | 7/1959 | Switzerland . |
| 991390 | 5/1965 | United Kingdom . |
| 1 580 444 | 12/1980 | United Kingdom . |
| 2 134 782 | 8/1984 | United Kingdom . |
| WO 93/06812 | 4/1993 | WIPO . |

OTHER PUBLICATIONS

STN International, Chemical Abstracts Service, Current Registry File Database Entry for "Essential Fatty Acids" Registry No. 11006–87–4.

Chemical Abstracts, vol. 55, No. 15, Published in Jul. 24, 1961, Abstract for Cited Swiss Patent 339,632 Provided by Applicants'.

Goodwin, T.W., "Biosynthesis of Vitamins and Related Copmounds", Academic Press, Published 1963, p. 232.

Martindale, The Extra Pharmacopoeia, 26th Edition, Blacow et al., Editors, Published in Jul. 1972, p. 1254.

Cousins et al., "Synthesis of 6–Fatty Acid Esters of L–Ascorbic Acid", The J. of the American Oil Chemists Society, 54(8), Aug. 1977, pp. 308–312.

Hassall et al., "Dihomo–Gamma–Linolenic Acid Reverses Hypertension Induced in Rats by Diet Rich in Saturated Fat", Lipids, 19(9), Published in 1984, pp. 699–703.

Begin et al., "Deficiency in Dietary Gamma–Linolenic and/or Eicosapentaenoic Acid May Determine Individual Susceptability to AIDS", Med.–Hypotheses, 20(1), Published in 1986, pp. 1–8. (Abstract).

McCollum, J.R., "FDA Alert on Evening Primrose Oil", J. of American Dietetic Association, vol. 89, No. 5, Issued May 1989, p. 622.

"Organic Chemistry" third edition 1984 p. 97, 22.1 Fatty Acids and Glyceryl Trialkanoates Derwent 1995 J59059612.

Datbase WPI Derwent AN 87–1409045 & JP–A–62081307.

Patent Abstracts of Japan vol. 17, No. 547 (C–1135) & JP–A–05 209 968.

Database WPI Derwent AN 93–308332 & JP–A–5 219 970.

Database WPI Derwent AN 91–167165 & JP–A–3 099 073.

Database WPI Derwent AN 89–141203 & JP–A–1 085 907.

Med Hypotheses vol. 5, No. 8, 1979 pp. 849–858 Horrobin "The regulation of prostaglandin E1 formation: a candidate for one of the fundamental mechanisms involved in the actions of vitamin C.".

*Primary Examiner*—Robert H. Harrison
*Attorney, Agent, or Firm*—Nixon & Vanderhye

[57] ABSTRACT

Ascorbyl-GLA or Ascorbyl-DGLA in medicaments for treatment of asthma and other disorders.

11 Claims, No Drawings

FATTY ACID DERIVATIVES

This is a Rule 62 File Wrapper Continuation of application Ser. No. 08/388,667, filed 17 Feb. 1995, now abandoned.

The invention relates to ascorbic acid (Vit. C) derivatives of fatty acids.

Ascorbic acid derivatives of fatty acids (1) are known, where R is a fatty acid chain and $R^1$=H or R.

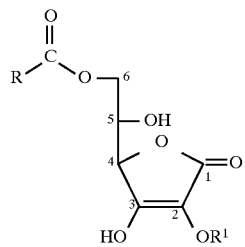

Thus Kaneko et al Arch. Biochm. Biophys. 304 No. 1,176–180, (1993) report protective action against the cytoxicity of linoleic acid hydroperoxide in human cell cultures, shown by 6-0-palmitoyl, 6-0-stearoyl and 2,6-0-dipalmitoyl ester and 2-0-octadecyl ether derivatives of ascorbic acid. Similarly the preparation of ascorbyl docosahexaenoate has been described.

Further, unsaturated fatty acids have been protected from atmospheric oxidation by ascorbic acid used with phosphorylated mono- or di-fatty acyl glycerides, the ascorbic acid optionally being in the form of a palmitate or stearate (Cloughley, EPA 93304827.4, based on UK 92 13322.2).

Also, the idea of co-administering gamma-linolenic acid (GLA) or dihomo-gamma-linolenic acid (DGLA) with ascorbic acid has been published in a number of previous applications by the inventors, for example EPA 0 019 423 and EPA 0 085 579.

Generally however little attention has been paid to ascorbate esters of fatty acids though Kanebo in JP-A-62 081307 discloses GLA esters of ascorbic acid in cosmetic compositions.

Ascorbic acid is of course well known as a water-soluble vitamin essential for health. Less remarked is the fact that ascorbic acid is able to stimulate the conversion of DGLA to prostaglandin $E_1$ ($PGE_1$). $PGE_1$ is a short lived substance which has an exceptionally wide range of desirable effects. It dilates blood vessels and bronchi and bronchioles, inhibits platelet aggregation, exerts anti-inflammatory effects, lowers cholesterol levels, lowers blood pressure, and is believed to have a range of other desirable actions including anti-cancer and anti-metastatic effects.

In view of the desirable effects of $PGE_1$ optimum conditions should exist for its formation in the body. One way of seeking to ensure this is to increase intake of DGLA or its immediate precursor GLA. Another is to provide appropriate levels of ascorbic acid to encourage the formation of $PGE_1$.

We now find that it is specifically advantageous to give GLA and DGLA as their ascorbic-6-acid esters subsequently referred to as Ascorbyl GLA and Ascorbyl DGLA. These compounds can be synthesised by the reaction of the acid chloride or anhydride of the fatty acid in the presence of a mineral acid catalyst i.e. hydrogen chloride, in a suitable solvent e.g. dimethyl acetamide/dichloromethane at a temperature between −10° C. and 30° C. as described herein. They have pharmaceutical uses in many conditions and the invention extends to their use in such conditions and in the preparation of medicaments for the purpose. The conditions include:

(a) asthma and related disorders, where $PGE_1$ is an effective and safe bronchodilator and anti-inflammatory agent and is likely to have a particularly desirable effect both in dilating airways and, in the longer term, suppressing the airway inflammation that is now recognised as a major factor in asthma (b) cardiovascular disorders associated with atherosclerosis, and/or elevated cholesterol, and/or hypertension, and/or excessive platelet aggregation (c) rheumatoid arthritis, osteoarthritis, dermatitis and other inflammatory disorders (d) cancer Uses also extend to cosmetic or skin care preparations and also to foods of any type but particularly nutritional supplements.

The particular valve of ascorbyl DGLA is the provision at the same time and in precisely the same place both the immediate substrate, DGLA, for $PGE_1$ biosynthesis and a stimulating agent, ascorbate which will enhance the conversion of the substrate DGLA to $PGE_1$. As far as we are aware the compound ascorbyl-DGLA has never previously been described.

The ester may be administered orally, enterally or parenterally in capsules, tablets, sachets, solutions, emulsions, powders, liposomes or other forms in doses of 0.1 mg to 50 g per day, preferably 10 mg to 10 g and very preferably 100 mg to 5 g per day. The ester may also be applied topically in creams, ointments, lotions, emulsions, pessaries, suppositories, sticks or other appropriate forms in which the compound is present in a concentration of 0.001% to 50%, preferably 0.1% to 20% and very preferably 1% to 10% by weight. Similar concentrations may be used to deliver aerosols, liposomes or other appropriate delivery systems which will ensure delivery of the drug directly to the airways.

A particular appropriate formulation is for the ester to be dissolved or dispersed in free fatty acids or triglycerides in which one or more of GLA, DGLA and/or the further anti-inflammatory fatty acid EPA is an important constituent preferably 5% or more by weight. Particularly suitable triglycerides are ones containing 1, 2 or 3 moieties selected from GLA, DGLA and EPA.

Synthesis Example

The Preparation of Ascorbic acid 6-(z,z,z-octadeca-6,9,12-trienoate) (Ascorbyl GLA; Ascorbyl DGLA may be prepared in the same way)

Hydrogen chloride gas (2.0 g) was bubbled into N,N-dimethyl acetamide (26.5 ml) at 0° C. To the resultant slurry was added a slurry of ascorbic acid (9.69 g) in dichloromethane (13.25 ml) and the mixture was stirred at 0° C. until solution occurred. To this solution at 0° C. under nitrogen, was added z,z,z-octadeca-6,9,12-trienoyl chloride (14.8 g) over a period of 4 hours and the resulting mixture was allowed to stand at the above temperature for 18 hours and room temperature for 1 hour. On cooling to 0° C., ethyl acetate (200 ml) and water (100 ml) was added and the mixture stirred for 1 hour. The organic layer was washed with brine (5×100 ml), dried ($Na_2SO_4$) and evaporated at 50° C./10 mmHg then 50° C./0.1 mm/4 hours to give ascorbic acid 6-[(z,z,z)-octadeca-6,9,12-trienoate] (18.25 g, 88%) as a pale yellow wax.

Use Examples

1. Tablets containing 50, 100, 250, 500 or 750 mg of Ascorbyl GLA or Ascorbyl DGLA either as such or with an appropriate excipient.

2. Soft gelatin or hard gelatin capsules containing 50, 100, 250 or 500 mg Ascorbyl GLA or Ascorbyl DGLA dissolved in free fatty acids enriched in GLA, DGLA or EPA or in triglycerides in which 1, 2 or 3 of the moieties are selected from GLA, DGLA or EPA.
3. Emulsion, powders, liquids, slurries, or solutions for oral, enteral or parenteral administration of Ascorbyl GLA or Ascorbyl DGLA in a concentration as referred to herein.
4. Ointments, creams, lotions, shampoos, or other appropriate formulations for the topical application of Ascorbyl GLA or Ascorbyl DGLA in a concentration as referred to herein.
5. Liposomes made using either phospholipids or glycolipids, for the oral, topical, parenteral or direct airway delivery of Ascorbyl-DGLA.
6. Sprays, suspensions, inhalers or other respiratory delivery systems containing Ascorbyl-DGLA.

We claim:

1. An orally adminstrable tablet or capsule consisting essentially of the ascorbic-6-acid ester of gamma-linolenic acid or the ascorbic-6-acid ester of dihomo-gamma-linolenic acid in association with a pharmaceutically acceptable carrier or diluent.

2. The tablet or capsule of claim 1 containing 0.001% to 50% by weight of the ester.

3. The tablet or capsule of claim 1 containing 0.1% to 20% by weight of the ester.

4. The tablet or capsule of claim 1 containing 1% to 10% by weight of the ester.

5. The tablet or capsule of claim 1 including an oil which contains at least 5% by weight of gamma-linolenic acid, dihomo-gamma-linolenic acid or an essential fatty acid in the free fatty acid form or triglyceride form.

6. A parenteral composition consisting essentially of the ascorbic-6-acid ester of gamma-linolenic acid or the ascorbic-6-acid ester of dihomo-gamma-linolenic acid in association with a pharmaceutically acceptable carrier or diluent.

7. The tablet/capsule/parenteral composition of claim 1 or 6 further including gamma-linolenic acid or dihomo-gamma-linolenic acid in free fatty acid or triglyceride form.

8. The composition of claim 6 containing 0.001% to 50% by weight of the ester.

9. The composition of claim 6 containing 0.1% to 20% by weight of the ester.

10. The composition of claim 1 including an oil which contains at least 1% to 10% by weight of the ester.

11. The composition of claim 6 further including an oil which contains at least 5% by weight of gamma-linolenic acid, dihomo-gamma-linolenic acid or an essential fatty acid in the free fatty acid form or triglyceride form.

* * * * *